(12) United States Patent
Gerber

(10) Patent No.: US 10,222,376 B2
(45) Date of Patent: Mar. 5, 2019

(54) METHODS AND COMPOSITIONS FOR IDENTIFYING LEUKEMIC STEM CELLS

(71) Applicant: The Charlotte Mecklenburg Hospital Authority, Charlotte, NC (US)

(72) Inventor: Jonathan M. Gerber, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 15/796,201

(22) Filed: Oct. 27, 2017

(65) Prior Publication Data

US 2018/0120321 A1    May 3, 2018

Related U.S. Application Data

(60) Provisional application No. 62/417,238, filed on Nov. 3, 2016.

(51) Int. Cl.
| | | |
|---|---|---|
| *G01N 33/68* | (2006.01) | |
| *A61K 39/00* | (2006.01) | |
| *G01N 33/574* | (2006.01) | |
| *C12Q 1/6886* | (2018.01) | |

(52) U.S. Cl.
CPC ..... *G01N 33/57426* (2013.01); *C12Q 1/6886* (2013.01); *C12Q 2600/112* (2013.01); *C12Q 2600/156* (2013.01); *G01N 2333/70596* (2013.01); *G01N 2333/90203* (2013.01); *G01N 2333/91148* (2013.01); *G01N 2333/96494* (2013.01)

(58) Field of Classification Search
None
See application file for complete search history.

(56) References Cited

U.S. PATENT DOCUMENTS

| 8,748,113 B2 | 6/2014 | Matsui et al. |
| 9,012,215 B2 | 4/2015 | Gerber et al. |
| 2013/0079424 A1 | 3/2013 | Gerber et al. |

OTHER PUBLICATIONS

Gerber et al (Blood, 119:3571-3577, 2012, IDS No. 9, filed Feb. 14, 2018 (Year: 2012).*
Kong et al (Leukemia 22:1207-1213, 2008, IDS No. 23, filed Feb. 14, 2018) (Year: 2008).*
Stanciu-Herrera et al (Leukemia Res, 32:625-632, 2008) (Year: 2008).*
Bonnet et al. "Human acute myeloid leukemia is organized as a hierarchy that originates from a primitive hematopoietic cell" *Nature Medicine* 3(7):730-737 (1997).
Cox et al. "Characterization of acute lymphoblastic leukemia progenitor cells" *Blood* 104(9):2919-2925 (2004).
Fluckiger et al. "In Vitro Reconstruction of Human B-Cell Ontogeny: From $CD34^+$ Multipotent Progenitors to Ig-Secreting Cells" *Blood* 92(12):4509-4520 (1998).
Gerber et al. "Characterization of chronic myeloid leukemia stem cells" *American Journal of Hematology* 86(1):31-37 (2011).
Gerber et al. "The Leukemic Stem Cell in Polycythemia Vera and Primary Myelofibrosis is Distinct From the Initiating JAK2 V617F-Positive Hematopoiertic Stem Cell" *Blood* 118(21):613 (2011) (Abstract Only).
Gerber et al. "A clinically relevant population of leukemic $CD34^+$ $CD38^-$ cells in acute myeloid leukemia" *Blood* 119(15):3571-3577 (2012).
Gerber et al. "Genome-wide comparison of the transcriptomes of highly enriched normal and chronic myeloid leukemia stem and progenitor cell populations" *Oncotarget* 4(5):715-728 (2013).
Gerber et al. "Single Cell Analysis of JAK2V617F Positive MPN Stem/Progenitor Cells in Chronic Phase and Leukemic Tranformation" *Blood* 122(21):1609 (2013).
Gerber et al. "Association of acute myeloid leukemia's most immature phenotype with risk groups and outcomes" *Haematologica* 101(5):607-616 (2016).
Gerber et al. "A Novel Approach to Identify a Putative Leukemia Stem Cell Population in Acute Lymphocytic Leukemia (ALL) and Distinguish Philadelphia Chromosome-Positive ALL from Lymphoid Blast Crisis Chronic Myeloid Leukemia" *Abstract for the American Society of Hematology's $58^{th}$ Annual Meeting & Exposition* (2 pages) (2016).
Ghiaur et al. "Cancer Stem Cells—Relevance to Clinical Transplantation" *Current Opinion in Oncology* 24(2):170-175 (2012).
Ghiaur et al. "Concise Review: Cancer Stem Cells and Minimal Residual Disease" *Stem Cells* 30(1):89-93 (2012).
Ghiaur et al. "Regulation of human hematopoietic stem cell self-renewal by the microenvironment's control of retinoic acid signaling" *Proceedings of the National Academy of Sciences* 110(40):16121-16126 (2013).
Gurney et al. Incidence of Cancer in Children in the United States. Sex-, race-, and 1-year age-specific rates by histologic type. *Cancer* 75(8):2186-2195 (1995).
Hann et al. "Determinants of outcome after intensified therapy of childhood lymphoblastic leukaemia: results from Medical Research Council United Kingdom acute lymphoblastic leukaemia XI protocol" *British Journal of Haematology* 113(1):103-114 (2001).
Hao et al. "In Vitro Identification of single $CD34^+CD38^-$ Cells With Both Lymphoid and Myeloid Potential" *Blood* 91(11):4145-4151 (1998).
Huff et al. "The paradox of response and survival in cancer therapeutics" *Blood* 107(2):431-434.
Jones et al. "Cancer Stem Cells: Are We Missing the Target" *Journal of the National Cancer Institute* 96(8):583-585 (2004).
Khalidi et al. "Acute Lymphoblastic Leukemia: Survey of Immunophenotype, French-American-British Classification, Frequency of Myeloid Antigen Expression, and Karyotypic Abnormalities in 210 Pediatric and Adult Cases" *American Society of Clinical Pathologists* 111(4):467-476 (1999).
Kong et al. "CD34+CD38+CD19+ as well as CD34+CD38−CD19+ cells are leukemia-initiating cells with self-renewal capacity in human B-precursor ALL" *Leukemia* 22(6):1207-1213 (2008).
Lapidot et al. "A cell initiating human acute myeloid leukemia after transplantation into SCID mice" *Nature* 367(6464):645-648 (1994).
Lazarus et al. "When, how, and what cell source for hematopoietic cell transplantation in first complete remission adult acute lymphoblastic leukemia?" *American Society of Hematology, Hematology, The Education Program* 2012(1):382-388 (2012).

(Continued)

Primary Examiner — Lei Yao
(74) Attorney, Agent, or Firm — Myers Bigel, P.A.

(57) ABSTRACT

The present invention provides methods and compositions for identifying leukemic stem cells.

2 Claims, 9 Drawing Sheets

(56) References Cited

OTHER PUBLICATIONS

Li et al. "Cancer incidence among children and adolescents in the United States, 2001-2003" *Pediatrics* 121(6):e1470-e1477 (2008) (Abstract Only).

Mrózek et al. "Cytogenetics and Molecular Genetics of Acute Lymphoblastic Leukemia" *Hematology/Oncology Clinics of North America* 23(5):991-1010 (2009).

Pui et al. "Acute Lymphoblastic Leukemia" *The New England Journal of Medicine* 339(9):605-615 (1998) (Abstract Only).

Pui et al. "Acute lymphoblastic leukemia" *Lancet* 371(9617):1030-1043 (2008) (Abstract Only).

Rehe et al. "Acute B lymphoblastic leukemia-propagating cells are present at high frequency in diverse lymphoblast populations" *EMBO Molecular Medicine* 5(1):38-51 (2012).

Sallan et al. "Myths and Lessons from the Adult/Pediatric Interface in Acute Lymphoblastic Leukemia" *American Society of Hematology, Hematology, the Education Program*: 128-132 (2006).

Schultz et al. "Risk- and response-based classification of childhood B-precursor acute lymphoblastic leukemia: a combined analysis of prognostic markers from the Pediatric Oncology Group (POG) and Children's Cancer Group (CCG)" *Blood* 109(3):926-935 (2007).

Siegel et al. "Cancer Statistics, 2012" *CA: A Cancer Journal for Clinicians* 62(1):10-29 (2012).

Arber et al. "Initial Diagnostic Workup of Acute Leukemia: Guideline From the College of American Pathologists and the American Society of Hematology" Arch Pathol Lab Med. (2017) 141: 1342-1393.

Arber et al. "The 2016 revision to the World Health Organization classification of myeloid neoplasms and acute leukemia" Blood (2016) 127(20):2391-2405.

Bernt et al. "Leukemia Stem Cells and Human Acute Lymphoblastic Leukemia" Seminars in Hematology (2009) 46(1):33-38.

Braig et al. "Resistance to anti-CD19/CD3 BiTE in acute lymphoblastic leukemia may be mediated by disruptec CD19 membrane trafficking" Blood (2017) 129(1):100-104.

Jackson et al. "Overcoming Antigen Escape with CAR T-cell Therapy" Cancer Discov (2015) 5:1238-1240.

Sotillo et al. "Convergence of Acquired Mutations and Alternative Splicing of CD19 Enables Resistance to CART-19 Immunotherapy" Cancer Discov Published OnlineFirst (2015) pp. OF2-OF14.

* cited by examiner

METHODS AND COMPOSITIONS FOR IDENTIFYING LEUKEMIC STEM CELLS

STATEMENT OF PRIORITY

This application claims the benefit, under 35 U.S.C. § 119(e), of U.S. Provisional Application Ser. No. 62/417,238, filed Nov. 3, 2016, the entire contents of which are incorporated by reference herein.

FIELD OF THE INVENTION

The present invention relates to methods and compositions for identifying leukemic stem cells.

BACKGROUND OF THE INVENTION

The identification of LSCs in acute lymphocytic leukemia (ALL) has proved challenging, as transplantation studies in immunocompromised mice have yielded conflicting results. The distinction between Philadelphia chromosome-positive (Ph+) ALL and lymphoid blast crisis (LBC) chronic myeloid leukemia (CML) is also controversial. Leukemia appears to retain some semblance of the normal hematopoietic hierarchical structure: i.e., rare leukemic stem cells (LSCs) with self-renewal capacity give rise to partially differentiated progeny that comprise the bulk of the leukemia but possess only limited proliferative potential. Existing therapies, although highly active against the leukemic bulk, are often ineffective against the hardier LSCs responsible for relapse. Therefore, a need exists for identifying LSCs in patients with a hematopoietic disorder that is not acute myelogenous leukemia (AML), such as ALL so that the patients can be identified as having a high or low risk for relapse and appropriate treatment can be delivered.

The present invention overcomes previous shortcomings by providing methods and compositions for identifying LSCs in patients with a hematopoietic disorder that is not AML, such as ALL.

SUMMARY OF THE INVENTION

In one embodiment, the present invention provides a method of identifying the presence of leukemic stem cells (LSCs) in a sample from a subject having or diagnosed with acute lymphocytic leukemia (ALL) or lymphoid blast crisis (LBC) chronic myeloid leukemia (CML), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating $CD34^+CD38^-$ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; and (g) identifying the cells of (f) that have an intermediate level of ALDH activity ($CD34^+CD38^-$ $ALDH^{int}$) in the sample from the subject when compared to the level of ALDH activity of the $CD34^+CD38^-$ cells in the reference sample as LSCs.

In another embodiment, the present invention provides a method of treating a subject having or diagnosed with acute lymphocytic leukemia (ALL) or lymphoid blast crisis (LBC) chronic myeloid leukemia (CML), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating $CD34^+CD38^-$ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; (g) identifying the cells of (f) that have an intermediate level of ALDH activity ($CD34^+CD38^-$ $ALDH^{int}$) in the sample from the subject when compared to the level of ALDH activity of the $CD34^+CD38^-$ cells in the reference sample as being LSCs; (h) administering to the subject a treatment for ALL or LBC CML; (i) repeating steps (a) through (f); and (j) determining that the subject has completed treatment for ALL or LBC CML when the presence of LSCs is not detected.

In a further embodiment, the present invention provides a method of distinguishing Philadelphia chromosome-positive (Ph+) ALL and lymphoid blast crisis (LBC) chronic myeloid leukemia (CML) in a subject, comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating $CD34^+CD38^-$ mononuclear cells of (c) using flow cytometry; (e) measuring the ALDH activity of the cells of (d); (f) comparing the levels of ALDH activity in the cells of (e) with the levels of ALDH activity in the cells of a reference sample; (g) identifying cells of (f) that have a high level of ALDH activity ($CD34^+CD38^-$ $ALDH^{high}$) in the sample from the subject when compared to the level of ALDH activity of the $CD34^+CD38^-$ cells in the reference sample; and h) assaying the $CD34^+CD38^-$ $ALDH^{high}$ cells identified in (g) for the presence or absence of a BCR/ABL mutation and/or the presence of CD7, CD10 and/or CD19 on the surface of the $CD34^+CD38^-$ $ALDH^{high}$ cells, wherein the presence of the BCR/ABL mutation and/or the presence of CD7, CD10 and/or CD19 on the surface of the $CD34^+CD38^-$ $ALDH^{high}$ cells identifies LBC CML in the subject and the absence of the BCR/ABL mutation and the absence of CD7, CD10 and CD19 on the surface of the $CD34^+CD38^-$ $ALDH^{high}$ cells identifies (Ph+) ALL in the subject.

In an additional embodiment, the present invention provides A method of guiding treatment of a subject having or diagnosed with acute lymphocytic leukemia (ALL) or lymphoid blast crisis (LBC) chronic myeloid leukemia (CML), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody, in combination with an anti-CD19 monoclonal antibody, an anti-CD 10 monoclonal antibody and/or an anti-CD7 monoclonal antibody; (d) isolating $CD34^+CD38^-$ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; and (g) identifying cells of (f) that have a high level of ALDH activity ($CD34^+$ $CD38^-$ $ALDH^{high}$) in the sample from the subject when compared to the level of ALDH activity of the $CD34^+CD38^-$ cells in the reference sample; and h) assaying the $CD34^+$ CD38⁻ ALDH$^{high}$ cells identified in (g) for the presence or absence of CD7, CD10 and/or CD19 on the surface of the CD34⁺CD38⁻ ALDH$^{high}$ cells, wherein the presence of CD7, CD10 and/or CD19 cells on the surface of the CD34⁺CD38⁻ ALDH$^{high}$ cells identifies the subject as being less likely to respond to chemotherapy alone relative to a subject lacking said cells; and (i) administering a treatment to the subject that is not chemotherapy alone.

In another embodiment, the present invention provides a method of identifying the presence of leukemic stem cells (LSC) in a sample from a subject having or diagnosed with a hematopoietic disorder, wherein the hematopoietic disorder is not acute myelogenous leukemia (AML), comprising: (a) obtaining a biological cell sample from the subject; (b) isolating CD34⁺CD38⁻ mononuclear cells from the sample; (c) measuring the ALDH activity of the cells of (b); and (d) identifying the cells of (c) that have an intermediate level of ALDH activity (CD34⁺CD38⁻ ALDH$^{int}$) relative to reference cells, as being LSCs.

In another embodiment, the present invention provides a method of identifying a subject having or diagnosed with a hematopoietic disorder as having an increased risk of relapse of a hematopoietic disorder, wherein the disorder is not AML, comprising: (a) treating the subject with the hematopoietic disorder that is not AML with a therapy; (b) obtaining a post-therapy biological cell sample from a subject; (c) isolating CD34⁺CD38⁻ mononuclear cells from the sample; (d) measuring the ALDH activity of the cells of (c); (e) identifying the cells of (c) that have am intermediate level of ALDH activity (CD34⁺CD38⁻ ALDH$^{int}$) as being LSC; and (f) determining that the subject has an increased risk of relapse of the hematopoietic disorder that is not AML, and/or requires further treatment, when the presence of LSCs are detected.

Also provided herein is a method of treating a subject having or diagnosed with a hematopoietic disorder that is not AML, comprising: (a) obtaining a pre- and/or post-therapy biological cell sample from a subject that has the hematopoietic disorder that is not AML; (b) isolating CD34⁺CD38⁻ mononuclear cells from the sample; (c) measuring the ALDH activity of the cells of (c); (d) identifying the cells of (c) that have an intermediate level of ALDH activity (CD34⁺CD38⁻ ALDH$^{int}$) as compared with reference cells as being LSCs; (e) treating the subject with a therapy for the hematopoietic disorder that is not AML; (f) repeating steps (a) to (e); and (g) determining that the subject has completed treatment for the hematopoietic disorder that is not AML when the presence of LSC is not detected.

In addition, the present invention provides a method of identifying the presence of leukemic stem cells (LSCs) in a sample from a subject having or diagnosed with a hematopoietic disorder that is not AML, comprising: (a) obtaining a biological cell sample from the subject; (b) isolating mononuclear cells from the sample of (a); (c) allowing the cells of (b) to take up a fluorescent substrate for the enzyme aldehyde dehydrogenase (ALDH) and labeling the cells with an anti-CD34 monoclonal antibody and an anti-CD38 monoclonal antibody; (d) isolating CD34⁺CD38⁻ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; and (g) identifying the cells of f) that have an intermediate level of ALDH activity (CD34⁺CD38⁻ ALDH$^{int}$) in the sample from the subject when compared to the level of ALDH activity of the CD34⁺CD38⁻ cells in the reference sample as being LSCs.

Furthermore, the present invention provides a method of identifying a subject as having an increased risk of relapse of a hematopoietic disorder that is not AML, comprising: (a) treating the subject having or diagnosed with the hematopoietic disorder that is not AML with a therapy for the hematopoietic disorder that is not AML; (b) obtaining a post-therapy biological cell sample from the subject; (c) allowing the cells of (b) to take up a fluorescence substrate for the enzyme aldehyde dehydrogenase (ALDH) and labeling the cells with a conjugated anti-CD34 monoclonal antibody and a conjugated anti-CD38 monoclonal antibody; (d) isolating CD34⁺CD38⁻ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; and (g) identifying the cells of (f) that have an intermediate level of ALDH activity (CD34⁺CD38⁻ ALDH$^{int}$) in the sample from the subject when compared to the level of ALDH activity of the CD34⁺CD38⁻ cells in the reference sample as being LSCs; and (h) identifying the subject as having an increased risk of relapse of the hematopoietic disorder that is not AML, and/or identifying the subject for further treatment for the hematopoietic disorder that is not AML, when the presence of LSCs is detected in the sample from the subject.

Additionally provided herein is a method of treating a subject having or diagnosed with a hematopoietic disorder that is not AML, comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating CD34⁺CD38⁻ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; (g) identifying the cells of (f) that have an intermediate level of ALDH activity (CD34⁺CD38⁻ ALDH$^{int}$) in the sample from the subject when compared to the level of ALDH activity of the CD34⁺CD38⁻ in the reference sample as being LSCs; (h) treating the subject with an therapy for the hematopoietic disorder that is not AML; (i) repeating steps (a) to (g); and (j) determining that the subject has completed treatment for the hematopoietic disorder that is not AML when the presence of LSCs is not detected.

DETAILED DESCRIPTION OF THE INVENTION

Figure 1:
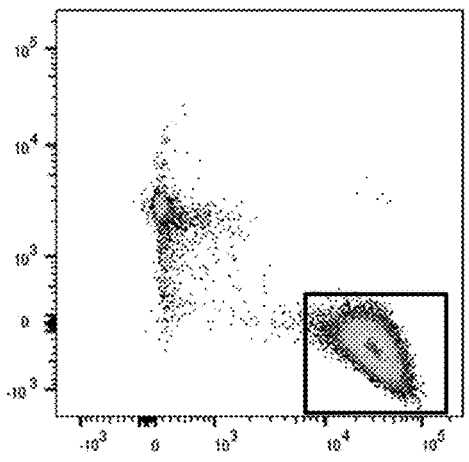
FIG. 1. Left: CD34+CD38− cells from a normal individual are displayed by ALDH and 7AAD. Nonviable cells are high in 7AAD and low in ALDH. Normal hematopoietic stem cells (HSCs) are ALDH$^{high}$ (box). No viable (7AAD negative) population of ALDH$^{int}$ cells is present. Center: Normal CD34+CD38− cells displayed by ALDH and CD19. None of the CD34+CD38− cells is positive for CD19. [Nonviable cells are low in ALDH; normal HSCs are ALDH$^{high}$ (box)]. Right: Normal CD34+CD38− cells displayed by ALDH and CD10. None of the CD34+CD38− cells is positive for CD10. [Nonviable cells are low in ALDH; normal HSCs are ALDH$^{high}$ (box)].
Figure 1:
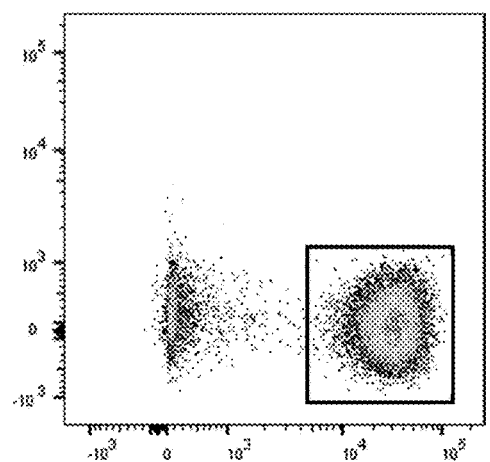
Figure 1:
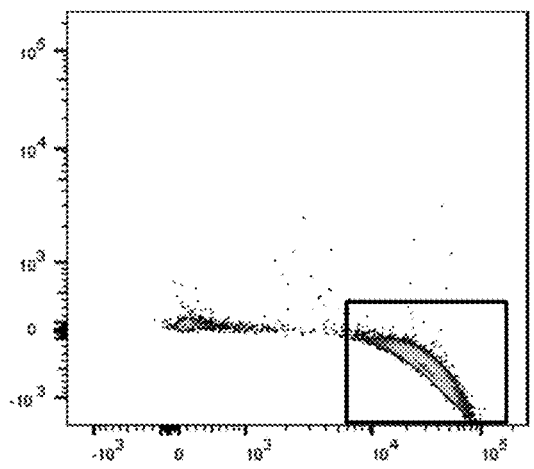

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a non-viral vector) and the like, is meant to encompass variations of ±20%, ±10%, ±5%, ±1%, ±0.5%, or even ±0.1% of the specified amount.

As used herein, the transitional phrase "consisting essentially of" (and grammatical variants) means that the scope of a claim is to be interpreted to encompass the specified materials or steps recited in the claim, "and those that do not materially affect the basic and novel characteristic(s)" of the claimed invention. Thus, the term "consisting essentially of" when used in a claim of this invention is not intended to be interpreted to be equivalent to "comprising."

Relapse of hematopoietic cell disorders that are not AML is thought to reflect the failure of current therapies to adequately target LSCs—the rare, resistant cells presumed responsible for maintenance of the hematopoietic disorders that are not AML, which are typically enriched in the $CD34^+CD38^-$ cell population. Despite research on LSCs over the past two decades, the clinical significance of these cells remains uncertain. However, LSCs would be expected to be enriched in minimal residual disease (MRD) and predictive of relapse of a hematopoietic cell disorder that is not AML.

Accordingly, the present invention is directed, in one aspect, to an assay technique capable of identifying LSCs in ALL and lymphoid blast crisis chronic myelogenous leukemia (LBC CML) and separating them from normal hematopoietic stem cells, on the basis of surface markers and activity of the enzyme, aldehyde dehydrogenase (ALDH). This assay can be used to: more accurately diagnose patients, track these cells, including determining responses to therapies (both standard and experimental), identify potential targets on these cells for new therapies, and isolate these cells for further research and analyses.

Currently available assays, which are typically flow cytometry and polymerase chain reaction (PCR)-based, only detect leukemia cells in general. There is no assay to detect LSCs in ALL or lymphoid blast crisis CML, or to reliably distinguish these diseases from one another.

Also, currently available assays cannot reliably determine whether patients with ALL are cured, particularly adult patients with the disease. Current research assays consist of using mouse engraftment studies to identify LSCs in these diseases and this represents a cumbersome, difficult to reproduce, and infeasible approach for clinical practice or even further research exploration.

It is theorized that the LSCs must be eradicated to achieve cure. Thus, the stem cell-based assay of this invention will be more accurate (both more sensitive and more specific) than existing methods in detecting residual leukemia after treatment and determining whether patients are truly cured. The proposed assay is capable of distinguishing ALL and lymphoid blast crisis CML from one another at a stem cell level and of separating LSCs from normal hematopoietic stem cells. The ability to identify LSCs provides a means to better research this population of cells, particularly with regard to developing and testing novel therapies to target these cells.

In some embodiments, the assay utilizes three basic markers to identify LSCs: CD34 (antibody-based stain), CD38 (antibody-based stain), and ALDH (ALDEFLUOR™ stain). In addition, these three markers can be further combined with other markers, such as CD19 and CD10, to better refine the LSC population. The proposed assay appears to be quite accurate at detecting minimal residual disease in patients who achieved clinical remission but subsequently relapsed.

The proposed assay appears capable of distinguishing ALL from lymphoid blast crisis CML (and likely blast crisis CML from chronic phase CML) in patients in whom this was not clear based on existing clinical parameters.

In some embodiments, the LSCs identified by the proposed assay appear to display both CD34 and CD19 on the surface in all of the ALL and lymphoid blast crisis CML cases analyzed thus far. The presence (or absence) of these markers on the LSCs in these diseases has been a point of controversy in the field.

In some embodiments, the proposed assay can be used to identify LSCs in ALL and lymphoid blast crisis CML. This ability lends itself to superior diagnostic accuracy in detecting low levels of the disease and in distinguishing these two diseases from one another (as well as from chronic phase CML). The assay also represents an ideal means to: separate LSCs from their normal counterparts (normal hematopoietic stem cells); identify novel therapeutic targets on the LSCs; test the efficacy of therapies against the LSCs; and detect any minimal residual disease at the LSC level (i.e., determine whether patients in remission are truly cured). This also represents a convenient research platform to further research the LSCs, to better understand leukemogenesis and develop means for early detection/prevention of these diseases.

As such, in some embodiments of the methods of the present invention, ALDH activity distinguishes normal from leukemic $CD34^+CD38^-$ cells which have both low ($ALDH^{low}$) and high ($ALDH^{high}$) levels of ALDH activity, and identifies those cells associated with relapse.

Thus, in one embodiment, the present invention provides a method of identifying the presence of leukemic stem cells (LSCs) in a sample from a subject having (or suspected of having) or diagnosed with acute lymphocytic leukemia (ALL) or lymphoid blast crisis (LBC) chronic myeloid leukemia (CML), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating CD34⁺CD38⁻ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; and (g) identifying the cells of (f) that have an intermediate level of ALDH activity (CD34⁺CD38⁻ ALDH$^{int}$) in the sample from the subject when compared to the level of ALDH activity of the CD34⁺CD38⁻ cells in the reference sample as LSCs.

In some embodiments, the above method can further comprise the step of assaying the cells of (d) for the presence or absence of CD3, CD5, CD7, CD10, CD19, CD20, CD22, CD25, CD33, CD40, CD42, CD44, CD45, CD47, CD90, CD96, CD123, CD133, CD138, CD235a, IL1RAP, PD1, and/or PDL1 on the cells. Such assaying for these cell markers can be carried out by various methods that are well known in the art and in some embodiments, the assaying would be carried out by contacting the cells with an antibody specific for the marker of interest, wherein the antibody has a detectable moiety. For example, the cells can be assayed for the presence of CD19 on the surface of said cells by contacting the cells with an anti-CD19 monoclonal antibody that is conjugated to a fluorescence moiety and analyzed by flow cytometry to determine the presence or absence of CD19 on the surface of the cells. The assay(s) can be employed to detect one or more than one (e.g., 2, 3, 4, 5, 6, 7, 8, 9, 10, etc.) marker, in any combination.

In a further embodiment, the present invention provides a method of treating a subject having (or suspected of having) or diagnosed with acute lymphocytic leukemia (ALL) or lymphoid blast crisis (LBC) chronic myeloid leukemia (CML), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating CD34⁺CD38⁻ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; (g) identifying the cells of (f) that have an intermediate level of ALDH activity (CD34⁺CD38⁻ ALDH$^{int}$) in the sample from the subject when compared to the level of ALDH activity of the CD34⁺CD38⁻ cells in the reference sample as being LSCs; (h) administering to the subject a treatment for ALL or LBC CML; (i) repeating steps (a) through (f); and (j) determining that the subject has completed treatment for ALL or LBC CML when the presence of LSCs is not detected. In this method, screening for the presence of detectable LSCs is carried out; treatment is administered and screening is carried out again. If LSCs are detected following treatment, further treatment is administered to the subject and a further screening is carried out. This process can be repeated until the results of the screening demonstrate no detectable LSCs, indicating that the treatment has been effective. Thus, the above method can further comprising repeating steps (a) through (g) and in some embodiments, through (h) until it has been determined that the treatment is complete by the lack of detectable LSCs.

In some embodiments, the above method can further comprise the step of assaying the cells of (d) for the presence or absence of CD3, CD5, CD7, CD10, CD19, CD20, CD22, CD25, CD33, CD40, CD42, CD44, CD45, CD47, CD90, CD96, CD123, CD133, CD138, CD235a, IL1RAP, PD1, and/or PDL1 on the cells. Such assaying for these cell markers can be carried out by various methods that are well known in the art and in some embodiments, the assaying would be carried out by contacting the cells with an antibody specific for the marker of interest, wherein the antibody has a detectable moiety. For example, the cells can be assayed for the presence of CD19 on the surface of said cells by contacting the cells with an anti-CD19 monoclonal antibody that is conjugated to a fluorescence moiety and analyzed by flow cytometry to determine the presence or absence of CD19 on the surface of the cells. The assay(s) can be employed to detect one or more than one (e.g., 2, 3, 4, 5, 6, 7, 8, 9, 10, etc.) marker, in any combination.

Non-limiting examples of a treatment of this invention include chemotherapy, drug therapy, immunotherapy, an antibody-based therapy, blood or marrow transplantation, hematopoietic stem cell transplantation, cellular therapy, targeted therapy, novel therapy, a tyrosine kinase inhibitor, a small molecule inhibitor, radiation therapy, and/or chimeric antigen receptor T cell therapy, and any combination thereof. It is further contemplated that any of these treatments can be excluded. It is also understood that any of these treatments can be carried out alone (i.e., in the absence of other treatments) or in any combination with other treatments.

The present invention further provides a method of distinguishing Philadelphia chromosome-positive (Ph+) ALL from lymphoid blast crisis (LBC) chronic myeloid leukemia (CML) in a subject (e.g., a subject in need of such distinguishing), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating CD34⁺CD38⁻ mononuclear cells of (c) using flow cytometry; (e) measuring the ALDH activity of the cells of (d); (f) comparing the levels of ALDH activity in the cells of (e) with the levels of ALDH activity in the cells of a reference sample; (g) identifying cells of (f) that have a high level of ALDH activity (CD34⁺CD38⁻ ALDH$^{high}$) in the sample from the subject when compared to the level of ALDH activity of the CD34⁺CD38⁻ cells in the reference sample; and h) assaying the CD34⁺CD38⁻ ALDH$^{high}$ cells identified in (g) for the presence or absence of a BCR/ABL mutation and/or the presence of CD7, CD10 and/or CD19 on the surface of the CD34⁺CD38" ALDH$^{high}$ cells, wherein the presence of the BCR/ABL mutation and/or the presence of CD7, CD10 and/or CD19 on the surface of the CD34⁺CD38⁻ ALDH$^{high}$ cells identifies LBC CML in the subject and the absence of the BCR/ABL mutation and the absence of CD7, CD10 and CD19 on the surface of the CD34⁺CD38⁻ ALDH$^{high}$ cells identifies (Ph+) ALL in the subject.

The steps of assaying the cells for the presence or absence of a BCR/ABL mutation and/or the presence or absence of CD7, CD10 and/or CD19 on the surface of cells can be carried out by well-known methods for detecting mutations, such as the BCR/ABL mutation, which is a well-documented mutation and by well-known methods for detecting cell surface markers.

In some embodiments, the above method can further comprise assaying the cells of (d) for the presence or absence of CD3, CD5, CD20, CD22, CD25, CD33, CD40, CD42, CD44, CD45, CD47, CD90, CD96, CD123, CD133, CD138, CD235a, IL1RAP, PD1, and/or PDL1 on the cells.

The assay(s) can be employed to detect one or more than one (e.g., 2, 3, 4, 5, 6, 7, 8, 9, 10, etc.) marker, in any combination.

In a further embodiment, the present invention provides a method of identifying new therapeutic targets for a subject having or diagnosed with acute lymphocytic leukemia (ALL) or lymphoid blast crisis (LBC) chronic myeloid leukemia (CML), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating CD34$^+$CD38$^-$ mononuclear cells or population of cells from the cells of (c) using flow cytometry; (e) measuring the ALDH activity of the cells or population of cells of (d); (f) comparing the levels of ALDH activity in the cells or population of cells from (e) with the levels of ALDH activity in the cells or population of cells from a reference sample; (g) identifying the cells of (f) that have an intermediate level of ALDH activity (CD34$^+$CD38$^-$ ALDH$^{int}$) or have a high level of ALDH activity (CD34$^+$CD38$^-$ ALDH$^{high}$) plus expression of particular markers (such as CD7, CD10, or CD19), in the sample from the subject when compared to the level of ALDH activity of the CD34$^+$CD38$^-$ cells in the reference sample as being LSCs; (h) comparing levels of potential therapeutic targets on the LSCs to the levels of these potential targets on residual normal hematopoietic stem cells (HSCs), which are CD34$^+$CD38$^-$ ALDH$^{high}$ cells lacking expression of particular markers, such as CD7, CD10, or CD19; and (i) based on these results, developing and/or administering to the subject a treatment for ALL or LBC CML, which can be but is not limited to chemotherapy, drug therapy, immunotherapy, antibody-based therapies, blood or marrow transplantation, hematopoietic stem cell transplantation, cellular therapy, targeted therapy, novel therapy, tyrosine kinase inhibitors, small molecule inhibitors, radiation therapy, and/or chimeric antigen receptor T cell therapy in any combination and/or to the exclusion of any recited treatment. Suitable or desirable targets are those markers and/or other molecules found on or in LSCs but not found on or in normal human stem cells (HSCs).

In an additional embodiment, the present invention provides a method of identifying a subject as having an increased risk of relapse of acute lymphocytic leukemia (ALL) or lymphoid blast crisis (LBC) chronic myeloid leukemia (CML) and/or identifying a subject in need of further treatment for ALL or LBC CML, comprising: (a) treating the subject having or diagnosed with ALL or LBC CML with an appropriate therapy; (b) obtaining a post-therapy biological cell sample from the subject; (c) allowing the cells of (b) to take up a fluorescence substrate for the enzyme aldehyde dehydrogenase (ALDH) and labeling the cells with a conjugated anti-CD34 monoclonal antibody and a conjugated anti-CD38 monoclonal antibody; (d) isolating CD34$^+$CD38$^-$ mononuclear cells or population of cells from the cells of (c) using flow cytometry; (e) measuring the ALDH activity of the cells or population of cells of (d); (f) comparing the levels of ALDH activity in the cells or population of cells from (e) with the levels of ALDH activity in the cells or population of cells from a reference sample; (g) identifying the cells or population of cells from (f) that have an intermediate level of ALDH activity (CD34$^+$CD38$^-$ ALDH$^{int}$) in the sample from the subject when compared to the level of ALDH activity of the CD34$^+$CD38$^-$ cells in the reference sample as being LSCs; and (h) identifying the subject as having an increased risk of relapse of the hematopoietic disorder, and/or identifying the subject as needing further treatment, when the presence of LSCs is detected in the sample from the subject.

Additionally provided herein is a method of guiding treatment of a subject having (or suspected of having) or diagnosed with acute lymphocytic leukemia (ALL) or lymphoid blast crisis (LBC) chronic myeloid leukemia (CML), comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody, in combination with an anti-CD19 monoclonal antibody, an anti-CD 10 monoclonal antibody and/or an anti-CD7 monoclonal antibody; (d) isolating CD34$^+$CD38$^-$ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; and (g) identifying cells of (f) that have a high level of ALDH activity (CD34$^+$CD38$^-$ ALDH$^{high}$) in the sample from the subject when compared to the level of ALDH activity of the CD34$^+$CD38$^-$ cells in the reference sample; and h) assaying the CD34$^+$CD38$^-$ ALDH$^{high}$ cells identified in (g) for the presence or absence of CD7, CD10 and/or CD19 on the surface of the CD34$^+$CD38$^-$ ALDH$^{high}$ cells, wherein the presence of CD7, CD10 and/or CD19 cells on the surface of the CD34$^+$CD38$^-$ ALDH$^{high}$ cells identifies the subject as being less likely to respond to chemotherapy alone relative to a subject lacking said cells; and (i) administering a treatment to the subject that is not chemotherapy alone. By "not chemotherapy alone," it is meant that the treatment can be chemotherapy in combination with other non-chemotherapy treatment(s) or the treatment can be non-chemotherapy treatment(s).

In some embodiments, the above method can further comprise assaying the cells of (d) for the presence or absence of CD3, CD5, CD20, CD22, CD25, CD33, CD40, CD42, CD44, CD45, CD47, CD90, CD96, CD123, CD133, CD138, CD235a, IL1RAP, PD1, and/or PDL1 on the cells. The assay(s) can be employed to detect one or more than one (e.g., 2, 3, 4, 5, 6, 7, 8, 9, 10, etc.) marker, in any combination.

In some embodiments, the present invention provides a method of identifying the presence of leukemic stem cells (LSCs) in a sample from a subject having or diagnosed with a hematopoietic disorder that is not AML, comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating CD34$^+$CD38$^-$ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; and (g) identifying the cells of (f) that have an intermediate level of ALDH activity (CD34$^+$CD38$^-$ ALDH$^{int}$) in the sample from the subject when compared to the level of ALDH activity of the CD34$^+$CD38$^-$ cells in the reference sample as being LSCs.

Furthermore, the present invention provides a method of identifying a subject as having an increased risk of relapse of a hematopoietic disorder that is not AML, comprising: (a)

treating the subject having or diagnosed with the hematopoietic disorder that is not AML with an appropriate therapy; (b) obtaining a post-therapy biological cell sample from the subject; (c) allowing the cells of (b) to take up a fluorescence substrate for the enzyme aldehyde dehydrogenase (ALDH) and labeling the cells with a conjugated anti-CD34 monoclonal antibody and a conjugated anti-CD38 monoclonal antibody; (d) isolating CD34$^+$CD38$^-$ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; (g) identifying the cells of (f) that have an intermediate level of ALDH activity (CD34$^+$CD38$^-$ ALDH$^{int}$) in the sample from the subject when compared to the level of ALDH activity of the CD34$^+$CD38$^-$ cells in the reference sample as being LSCs; and (h) identifying the subject as having an increased risk of relapse of the hematopoietic disorder that is not AML, and/or identifying the subject for further treatment, when the presence of LSCs is detected in the sample from the subject.

In addition, the present invention provides a method of treating a subject having or diagnosed with a hematopoietic disorder that is not AML, comprising: (a) obtaining a biological cell sample from the subject; (b) isolating mononuclear cells from the sample of (a); (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody; (d) isolating CD34$^+$CD38$^-$ mononuclear cells from the cells of (c) using flow cytometry; (e) measuring the ALDH activity of the cells of (d); (f) comparing the levels of ALDH activity in the cells of (e) with the levels of ALDH activity in the cells of a reference sample; (g) identifying the cells of (f) that have an intermediate level of ALDH activity (CD34$^+$CD38$^-$ ALDH$^{int}$) in the sample from the subject when compared to the level of ALDH activity of the CD34$^+$CD38$^-$ in the reference sample as being LSCs; (h) treating the subject with an appropriate therapy; (i) repeating steps (a) to (g); and (j) determining that the subject has completed treatment when the presence of LSCs is not detected. In some embodiments, the method can further comprise repeating steps (a) through (h) if the presence of LSCs is detected.

In the methods described herein, the hematopoietic disorder that is not AML can be acute lymphocytic leukemia (ALL), chronic myeloid leukemia (CML), chronic phase CML, accelerated phase CML, lymphoid blast crisis CML, myeloid blast crisis CML, myelodysplastic syndrome, chronic myelomonocytic leukemia (CMML), juvenile myelomonocytic leukemia (JMML), chronic neutrophilic leukemia (CNL), myeloproliferative neoplasm, essential thrombocytosis, polycythemia vera, myelofibrosis, mastocytosis, hypereosinophilic syndrome, chronic lymphocytic leukemia (CLL), paroxysmal nocturnal hemoglobinuria (PNH) and any combination thereof. In embodiments of this invention, the hematopoietic disorder is not AML. It is contemplated that any of the hematopoietic disorders can excluded from embodiments of this invention, singly or in any combination.

As used herein, the term ALDH$^{int}$ means CD3$^{4+}$CD3$^{8-}$ cells having an intermediate level of ALDH activity relative to the ALDH levels of reference cells, which can have low or high ALDH activity.

Markers that can be detected or not detected on the surface of a cell of this invention according to the methods described herein include, but are not limited to, CD3, CD5, CD10, CD19, CD20, CD22, CD25, CD33, CD40, CD42, CD45, CD47, CD90, CD96, CD123, CD133, CD138, CD235a, CD9, CD44, CD61, CD69, PD1, PDL1, and any other cell surface markers or markers of cell differentiation now known or later identified.

As used herein, the term "isolating" with regard to, e.g., the CD34$^+$ cells includes separating the cells from the biological sample, which can be performed using any well known means in the art. In an embodiment, the separation is performed using a ficoll gradient and centrifugation, followed by enrichment using a CD34$^+$ antibody column or similar means.

The CD34$^+$ cells can be labeled using any known labeled conjugate to anti-CD34 and anti-CD38 antibodies, where the conjugates have detectable labels that can be differentiated from each other. In some embodiments, the CD34$^+$ cells can be labeled with monoclonal phycoerythrin-conjugated anti-CD34 antibody and allophycocyanin (APC)-conjugated anti-CD38 antibody, respectively, which fluoresce at different wavelengths. Thus, in some embodiments, the anti-CD34 monoclonal antibody is conjugated to phycoerythrin and in some embodiments, the anti-CD38 monoclonal antibody is conjugated, with all phycocyanin. Any antibodies of this invention, directed to any of the markers of this invention can be monoclonal antibodies and any antibody of this invention can be linked or conjugated to a detectable label or moiety.

By "detectable label or moiety" is meant a composition that when linked to a molecule of interest renders the latter detectable, via, e.g., spectroscopic, photochemical, biochemical, immunochemical, and/or chemical means. For example, useful labels include radioactive isotopes, magnetic beads, metallic beads, colloidal particles, fluorescence dyes, electron-dense reagents, enzymes (for example, as commonly used in an ELISA), biotin, digoxigenin, or haptens.

To assess ALDH activity of the CD34$^+$ cells, the cells can be contacted with a fluorescence ALDH substrate which is taken up by the cells, wherein ALDH cleaves the substrate and allows the fluorescence compound to be retained in the intact living cell where it can be detected using a fluorimeter or fluorescence cell sorter (FACS) device. In an embodiment, the CD34$^+$ cells are labeled using ALDEFLUOR™ fluorescence reagent, which comprises a biodipy fluorescence ligand attached to aminoacetate. It will be understood by those of skill that any similar labeled substrate can be used with the methods of the present invention.

Those of ordinary skill in the art will understand that the order in which the CD34$^+$ cells are labeled for ALDH activity and then labeled to detect CD34$^+$ and CD38$^-$ cells is not significant. The cells can be labeled in any order as long as all of the labeling is completed before detection and analysis.

It will be understood that the methods of the present invention that determine the ALDH activity of the CD34$^+$CD38$^-$ cells are useful in preclinical research activities as well as in clinical research in various diseases or disorders, including, for example, acute lymphocytic leukemia (ALL), chronic myeloid leukemia (CML, to include chronic phase, accelerated phase, lymphoid blast crisis, and myeloid blast crisis), myelodysplastic syndrome, chronic myelomonocytic leukemia (CMML), juvenile myelomonocytic leukemia (JMML), chronic neutrophilic leukemia (CNL), myeloproliferative neoplasms (including, e.g., essential thrombocytosis, polycythemia vera, myelofibrosis), mastocytosis, hypereosinophilic syndrome, and chronic lymphocytic leukemia (CLL), as well as any other clonal hematopoietic disorder other than AML now known or later identified.

The methods of the present invention can identify those subjects who require further treatment (i.e., those in whom the ALDH$^{int}$ cells persist); this may also serve as an early surrogate for leukemia-free survival.

In accordance with an embodiment, the present invention provides methods that allow LSCs to be viably isolated and distinguished from normal HSCs. As described herein, the inventive methods allow for identification of putative therapeutic targets and can be used to simultaneously assess a therapy's toxicity against normal hematopoietic stem cells while assessing its effectiveness against LSCs.

In accordance with another embodiment, the present invention provides a method for prediction of an increased risk of relapse after treatment in a subject having or diagnosed with a hematopoietic disorder that is not AML, comprising: (a) treating the subject with an appropriate therapy; (b) obtaining a post-therapy biological sample from a subject; (c) isolating CD34$^+$CD38$^-$ mononuclear cells or population of cells from the sample; (d) measuring the ALDH activity of the cells or population of cells of (c); (e) identifying the cells from (d) that have an intermediate level of ALDH activity (CD34$^+$CD38$^-$ ALDHn as being LSCs; and (f) determining that the subject has an increased risk of relapse of the hematopoietic disorder that is not AML, and/or requires further treatment, when the presence of LSCs is detected.

The inventive methods can be used to assist in the clinical assessment of patients having a hematopoietic disorder that is not AML who have undergone treatment, including chemotherapeutic treatment or bone marrow ablation and transplantation, to determine if there is any identifiable population of LSC, based on detection and/or presence of CD34$^+$CD38$^-$ ALDH$^{int}$ cells in one or more biological cell samples from the patient. These methods can be used to periodically reassess the patients to monitor the course of treatment and/or treatment outcome over time.

In accordance with a further embodiment, the present invention provides a method for treatment of a subject having or diagnosed with a hematopoietic disorder that is not AML, comprising: (a) obtaining a pre- and/or post-therapy biological sample from a subject; (b) isolating CD34$^+$CD38$^-$ mononuclear cells from the sample; (c) measuring the ALDH activity of the cells of (b); (d) identifying the cells from (c) that have an intermediate level of ALDH activity (CD34$^+$CD38$^-$ ALDH$^{int}$) as being LSCs; (e) treating the subject with an appropriate therapy; (f) repeating steps (a) to (e); and (g) determining that the subject has completed treatment for the hematopoietic disorder that is not AML when the presence of LSCs is not detected.

The inventive methods can also be used to help choose the type of treatment a patient having a hematopoietic disorder that is not AML may receive and can be also used to clinically assess whether the treatment being used is effective.

The methods of this invention can also be used to identify new potential therapeutic targets on LSCs in the diseases and disorders of this invention.

The methods of this invention can also be used to determine which subjects have diseases that are only curable at present with an allogeneic hematopoietic stem cell transplant (i.e., those with ALDH high LSCs).

The phrase "reference sample," "control or control sample" or "normal" refers to any standard or reference tissue or material that has not been identified as being present in, or associated with, a hematopoietic disorder. For example, in methods of this invention employing samples from subjects that have or are diagnosed with ALL or LBC CML, the reference or control sample can be from a subject that is known not to have ALL or LBC CML. In some embodiments, a reference or control sample can be from a healthy subject (e.g., a subject not known to have any hematopoietic disorder) or from a subject that is not known to have the hematopoietic disorder of interest in the methods of this invention.

The term "biologically active" as used herein means an enzyme or protein having structural, regulatory, or biochemical functions of a naturally occurring molecule.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. A subject of this invention can be any subject that is susceptible to a hematopoietic disorder that is not AML and in particular embodiments, the subject of this invention is a human subject.

A "subject in need thereof" or "a subject in need of" is a subject known to have, or is suspected of having or developing a hematopoietic disorder that is not AML, such as ALL or LBC CML.

An "appropriate therapy" or "therapy" for the treatment of a hematopoietic disorder of this invention that is not AML includes therapies well known in the art, including but not limited to, chemotherapy, radiation, targeted small molecules (e.g., tyrosine kinase inhibitors), immunotherapy, hematopoietic stem cell transplantation and any combination thereof.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

Additionally as used herein, the terms "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

"Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

A composition of the present invention (e.g., a pharmaceutical composition) may contain one or more excipients or adjuvants. Selection of excipients and/or adjuvants and the amounts to use may be readily determined by the formulation scientist upon experience and consideration of standard procedures and reference works in the field.

By "parenteral" is meant intravenous, subcutaneous or intramuscular administration. In the methods of the present invention, the composition or compound may be administered alone, simultaneously with one or more other compounds, or the composition and/or compounds may be administered sequentially, in either order. It will be appreciated that the actual method and order of administration will vary according to, inter alia, the particular preparation of compound(s) being utilized, the particular formulation(s) of the one or more other compounds being utilized, and the conditions to be treated. The optimal method and order of administration of the compounds of the disclosure for a given set of conditions can be ascertained by those skilled in the art using conventional techniques and in view of the information set out herein.

In prophylactic applications, pharmaceutical compositions or medicaments are administered to a subject susceptible to, or otherwise at risk of, occlusion or narrowing of an artery and/or its branches and/or a disease, disturbance and/or pathological condition of an artery and/or its branches in an amount sufficient to eliminate or reduce the risk, lessen the severity, or delay the onset, including biochemical, histologic and/or physiologic symptoms. In therapeutic applications, compositions or medicaments are administered to a subject suspected of, or already having, occlusion or narrowing of an artery and/or its branches and/or has had or is having a disease, disturbance and/or pathological condition of an artery and/or its branches in an amount sufficient to treat, or at least partially reduce or arrest, the symptoms (biochemical, histologic and/or physiological). An amount adequate to accomplish therapeutic or prophylactic treatment is defined as an effective amount or a therapeutically or prophylactically effective dose. In either prophylactic or therapeutic regimens, compounds and/or compositions of the present invention can be administered in several doses until a desired effect has been achieved.

An effective dose or effective doses of the compositions of the present invention, for the treatment of the conditions described herein can vary depending upon many different factors, including means of administration, target site, physiological state of the subject, whether the subject is human or an animal, other medications administered, and/or whether treatment is prophylactic or therapeutic. In some embodiments, the subject is a human but nonhuman mammals including transgenic mammals can also be treated. Treatment dosages can be titrated to optimize safety and efficacy. Generally, an effective amount of the compositions of this invention will be determined by the age, weight and condition or severity of disease or disorder of the subject.

Generally, dosing (e.g., an administration) can be one or more times daily, or less frequently, such as once a day, once a week, once a month, once a year, to once in a decade, etc. and may be in conjunction with other compositions as described herein.

The dosage and frequency of administration can vary depending on whether the treatment is prophylactic or therapeutic. In prophylactic applications, a relatively low dosage can be administered at relatively infrequent intervals over a long period of time. In therapeutic applications, a relatively high dosage at relatively short intervals is sometimes appropriate until severity of the injury is reduced or terminated, and typically until the subject shows partial or complete amelioration of symptoms of injury. Thereafter, the subject can be administered a prophylactic regimen.

The terms "increased risk" and "decreased risk" as used herein define the level of risk that a subject has of having a relapse of a hematopoietic disorder that is not AML, as compared to a control subject.

A sample of this invention can be biological sample that comprises or is made up of cells of this invention, nonlimiting examples of which can include hematopoietic cells from blood, bone marrow, etc.

The present invention further provides a kit of reagents to carry out the steps of the methods described herein.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including patent publications, non-patent publications, patent applications, and patents, cited herein are hereby incorporated by reference to the same extent as if each reference were individually and specifically indicated to be incorporated by reference and were set forth in its entirety herein.

The present invention is more particularly described in the following examples that are intended as illustrative only since numerous modifications and variations therein will be apparent to those skilled in the art.

The following examples provide illustrative embodiments. Certain aspects of the following examples are disclosed in terms of techniques and procedures found or contemplated by the present inventors to work well in the practice of the embodiments. In light of the present disclosure and the general level of skill in the art, those of skill will appreciate that the following examples are intended to be exemplary only and that numerous changes, modifications, and alterations can be employed without departing from the scope of the presently claimed subject matter.

EXAMPLES

Example 1

Identification of a Putative Leukemia Stem Cell Population in Acute Lymphocytic Leukemia (ALL) and Distinguishing Philadelphia Chromosome-Positive ALL from Lymphoid Blast Crisis Chronic Myeloid Leukemia (LBC CML)

Introduction. The identification of LSCs in acute lymphocytic leukemia (ALL) has proved challenging, as transplantation studies in immunocompromised mice have yielded conflicting results. The distinction between Philadelphia chromosome-positive (Ph+) ALL and lymphoid blast crisis (LBC) chronic myeloid leukemia (CML) is also controversial.

Methods. Bone marrow and/or peripheral blood specimens were collected at diagnosis from patients with B cell ALL or LBC CML on an IRB-approved protocol. A total of 7 patients was evaluated: 2 Ph– ALL, 2 Ph+ ALL, and 3 LBC CML patients. $CD34^+$ cells were isolated by magnetic bead and column selection and then analyzed by flow cytometry with respect to CD38 expression and ALDH activity. Sorted cell populations were analyzed by fluorescence in situ hybridization (FISH) for leukemia-specific abnormalities. Polymerase chain reaction (PCR) was performed on clinical samples to determine the presence of a p190 vs. p210 transcript.

Results. All patients harbored an aberrant $CD34^+CD38^-ALDH^{int}$ population. This population was ≥95% positive for BCR/ABL by FISH in all Ph+ ALL and LBC CML cases. It was similarly positive (≥75%) for other leukemia-specific FISH abnormalities (including trisomy 4, 8, 10, 12, and/or 21) in all four ALL cases, as well as one LBC CML case. Conversely, the $CD34^+CD38^-ALDH^{high}$ population (which typically contains the normal HSCs) lacked any of the other cytogenetic abnormalities in all of the cases, irrespective of Ph status or a diagnosis of ALL vs. CML. Notably, the $CD34^+CD38^-ALDH^{high}$ population was negative for BCR/ABL in the Ph+ ALL cases but was >95% positive for BCR/ABL by FISH in the LBC CML cases. The B cell differentiation marker, CD19, was expressed on the $CD34^+CD38^-ALDH^{int}$ but not the $CD34^+CD38^-ALDH^{high}$ population in all ALL cases, both Ph– and Ph+. In contrast, CD19 expression was variable in the LBC CML cases. Both Ph+ ALL cases possessed a p190 BCR/ABL transcript, whereas all of the LBC CML cases contained a p210 transcript. Also of note, the $CD34^+CD38^-ALDH^{int}$ population was persistently detectable in one of the LBC CML patients while in complete remission after induction therapy and that patient subsequently relapsed.

Conclusions. An abnormal $CD34^+CD38^-ALDH^{int}$ population was identified in all cases of B cell ALL and LBC CML. The $CD34^+CD38^-ALDH^{high}$ population was normal by FISH in the ALL cases but contained the BCR/ABL mutation in the LBC CML cases, thus permitting distinction between Ph+ ALL and LBC CML (which also differed based on the presence of p190 vs. p210 transcripts, respectively). Additionally, clonal evolution from chronic phase to lymphoid blast crisis CML was apparent, based on the acquisition of additional cytogenetic abnormalities unique to the $CD34^+CD38^-ALDH^{int}$ population as compared to the $CD34^+CD38^-ALDH^{high}$ population. The presence of CD19 on the putative LSCs in the 4 cases of ALL suggests that CD19-directed therapies may target the LSCs and thus may have curative potential. This assay may serve as a means to evaluate other possible therapeutic targets. Lastly, the detection of the abnormal CD34$^+$CD38$^-$ALDH$^{int}$ population may have utility as a minimal residual disease assay for monitoring response to treatment.

Example 2

Introduction. The identification of LSCs in acute lymphocytic leukemia (ALL) has proved challenging, as transplantation studies in immunocompromised mice have yielded conflicting results. The distinction between Philadelphia chromosome-positive (Ph+) ALL and lymphoid blast crisis (LBC) chronic myeloid leukemia (CML) is also controversial.

Methods. Bone marrow and/or peripheral blood specimens were collected from normal donors and from patients with ALL or LBC CML on an IRB-approved protocol. A total of 22 patients was evaluated at diagnosis or relapse: 8 Ph− B-cell ALL, 8 Ph+ ALL, 1 T-cell ALL, and 5 LBC CML patients. Additional patients were evaluated while in remission after therapy. CD34$^+$ cells were isolated by magnetic bead and column selection. Samples were analyzed by flow cytometry with respect to CD34, CD38, CD19, and CD10 expression, as well as ALDH activity. Sorted cell populations were analyzed by fluorescence in situ hybridization (FISH) for leukemia-specific abnormalities. Polymerase chain reaction was performed on clinical samples to determine the presence of a p190 vs. p210 transcript in BCR/ABL positive cases.

Figure 2:
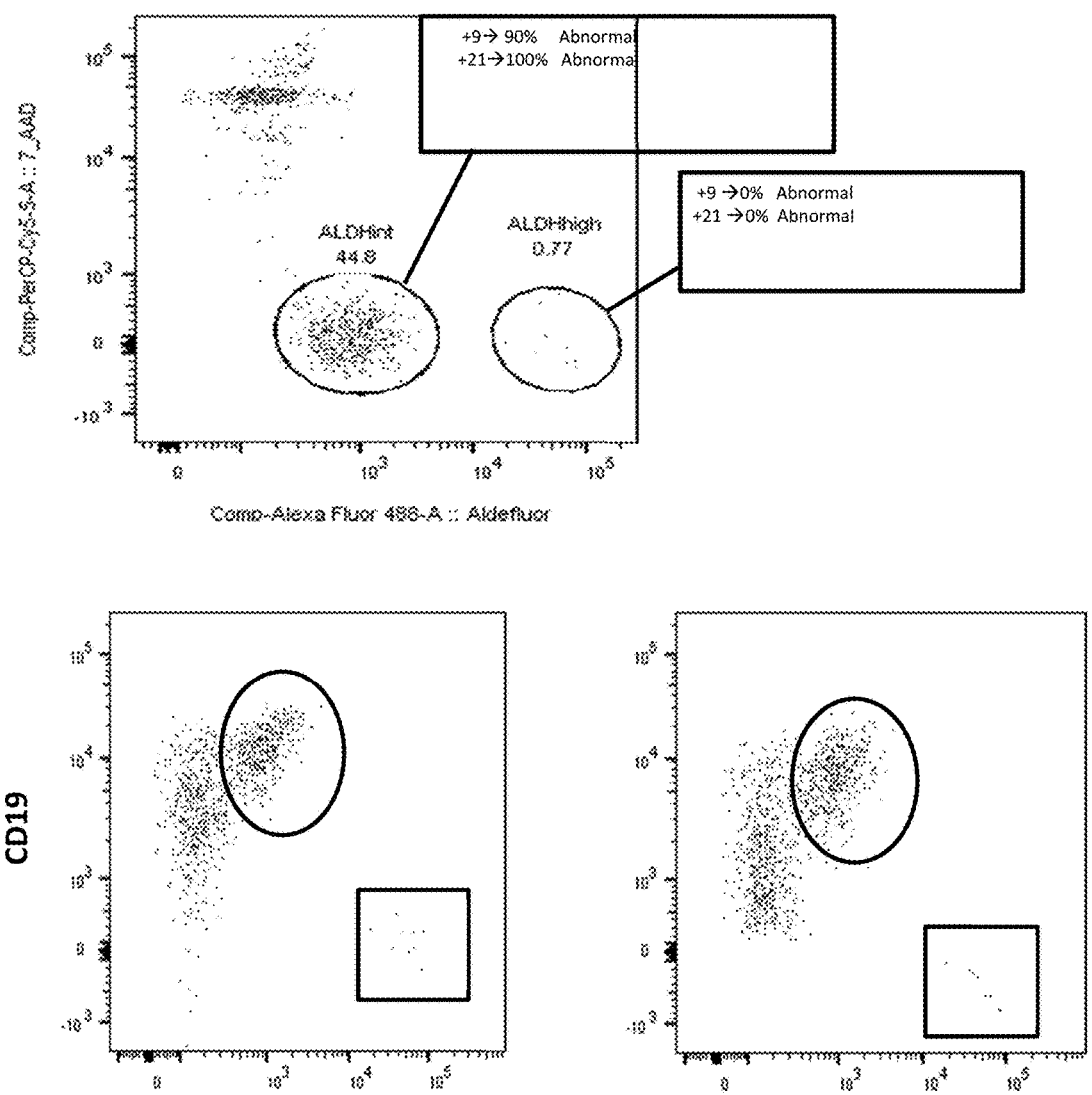
FIG. 2. Top: CD34+CD38− cells from a patient with Ph−ALL, displayed by ALDH and 7AAD (cells which are high in 7AAD and low in ALDH are nonviable). A viable, abnormal population of ALDH$^{int}$ cells (representing the putative ALL stem cell) is present, which is 90% positive for an extra copy of chromosome 9 (+9) and 100% positive for an extra copy of chromosome 21 (+21) by FISH. In contrast, the ALDH$^{high}$ population (representing residual normal hematopoietic stem cells) is normal for both chromosomes 9 and 21 by FISH. Bottom Left: CD34+CD38− cells displayed by ALDH and CD19. The CD34+CD38− ALDH$^{int}$ putative LSCs are positive for CD19 (circled), whereas the CD34+CD38− ALDH$^{high}$ normal HSCs (box) lack CD19. Bottom Right: CD34+CD38− cells displayed by ALDH and CD10. The CD34+CD38− ALDH$^{int}$ putative LSCs are positive for CD10 (circled), whereas the CD34+CD38− ALDH$^{high}$ normal HSCs (box) lack CD10.
Figure 3:
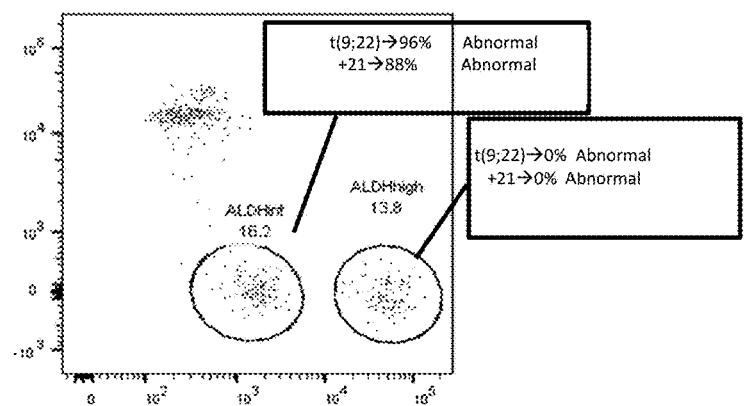
FIG. 3. Top: CD34+CD38− cells from a patient with Ph+ ALL, displayed by ALDH and 7AAD (cells which are high in 7AAD and low in ALDH are nonviable). A viable, abnormal population of ALDH$^{int}$ cells (representing the putative ALL stein cell) is present, which is 96% positive for the Philadelphia chromosome (t(9;22)) and 88% positive for an extra copy of chromosome 21 (+21) by FISH. In contrast, the ALDH$^{high}$ population (representing residual normal HSCs) is normal for both t(9;22) and +21 by FISH. Bottom Left: CD34+CD38− cells displayed by ALDH and CD19. The CD34+CD38− ALDH$^{int}$ putative LSCs are positive for CD19 (circled), whereas the CD34+CD38− ALDH$^{high}$ normal HSCs (box) lack CD19. Bottom Right: CD34+CD38− cells displayed by ALDH and CD10. The CD34+CD38− ALDH$^{int}$ putative LSCs are positive for CD10 (circled), whereas the CD34+CD38− ALDH$^{high}$ normal HSCs (box) lack CD10.
Figure 3:
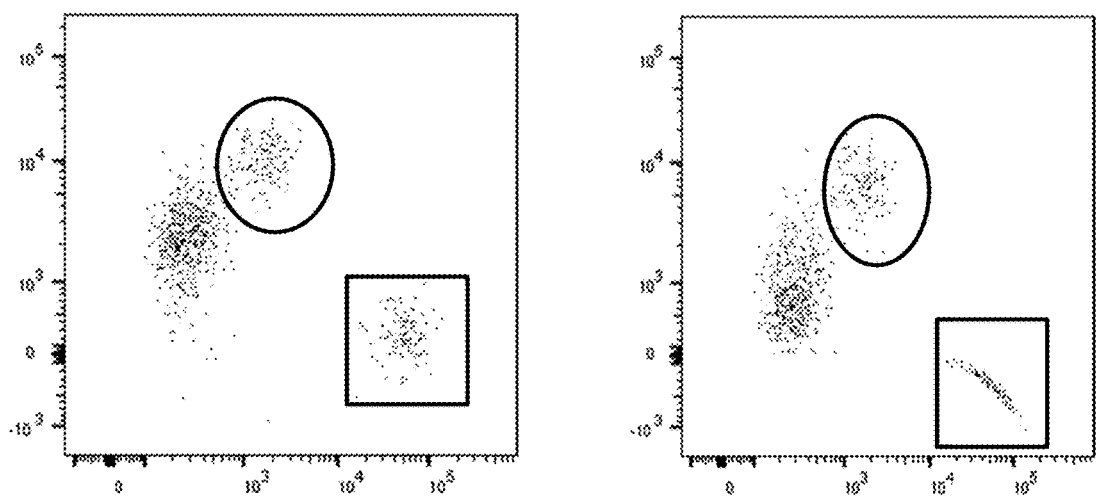
Figure 4:
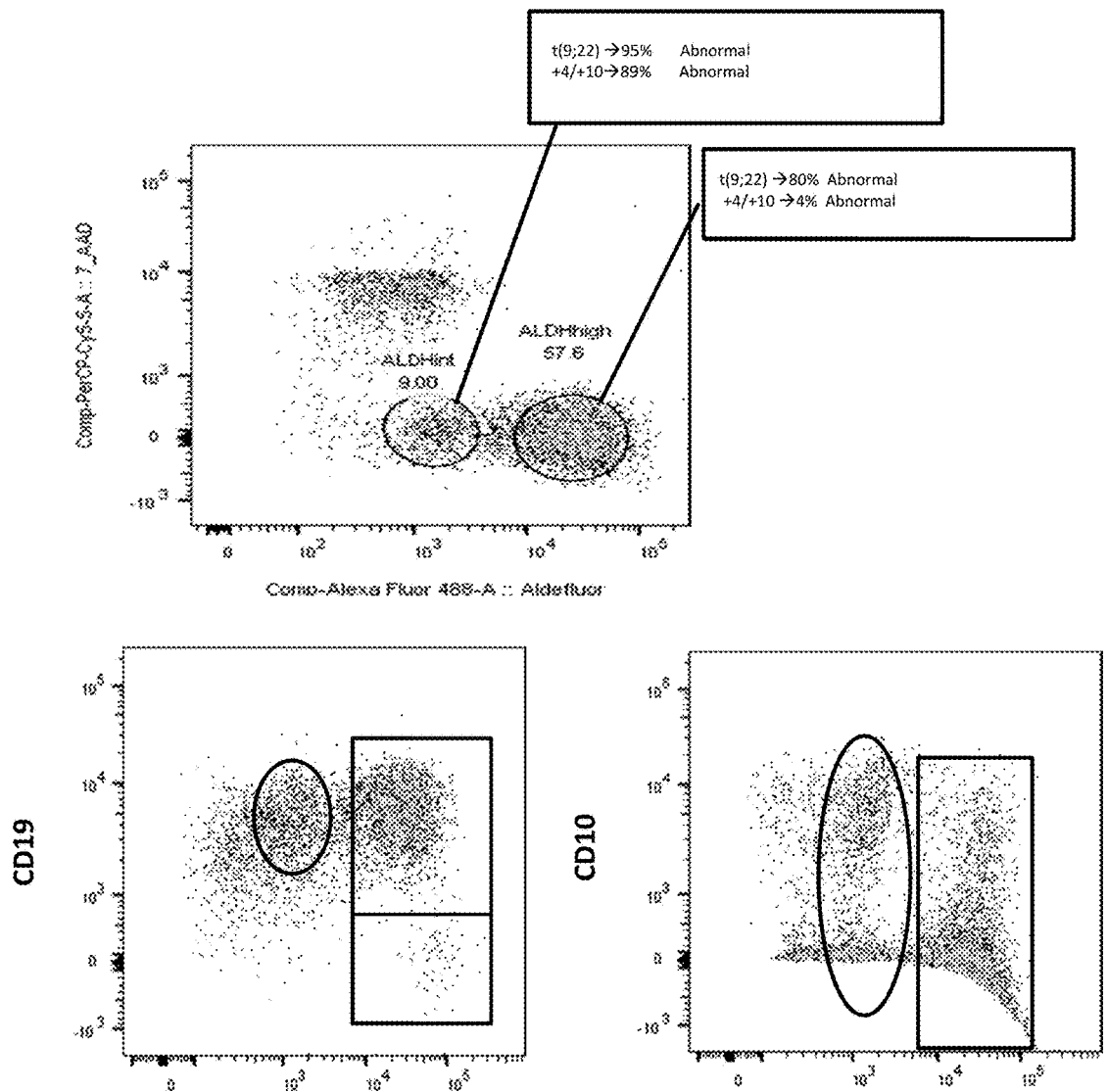
FIG. 4. Top: CD34+CD38− cells from a patient with lymphoid blast crisis CML, displayed by ALDH and 7AAD (cells which are high in 7AAD and low in ALDH are nonviable). A viable, abnormal population of ALDH$^{int}$ cells is present, which is 95% positive for the Philadelphia chromosome (t(9;22)) and 89% positive for an extra copy of chromosome 4 and/or 10 (+4/+10) by FISH. The ALDH$^{high}$ population is 80% positive t(9;22), but essentially lacks the +4/+10 (at only 4%) by FISH. Thus, there appears to be clonal evolution from the ALDH$^{int}$ to the ALDH$^{high}$ population. Most of both the CD34+CD38− ALDH$^{int}$ and the CD34+CD38− ALDH$^{high}$ cell populations are positive for CD19. A subset of the CD34+CD38− ALDH$^{int}$ population is positive for CD10, whereas most of the CD34+CD38− ALDH$^{high}$ cells lack CD10. Bottom Left: CD34+CD38− cells displayed by ALDH and CD19. The CD34+CD38− ALDH$^{int}$ putative LSCs are positive for CD19 (circled). Most of the CD34+CD38− ALDH$^{high}$ population (upper box) is also positive for CD19. These ALDH$^{high}$CD19+ cells appear to represent a "chronic phase" leukemia stem cell, with further evolution to an ALDH$^{int}$CD19+"blast crisis" stem cell population, which gains+4/+10, in addition to t(9;22). A subset of the CD34+CD38− ALDH$^{high}$ population (lower box) lacks CD19, likely representing residual normal HSCs. Bottom Right: CD34+CD38− cells displayed by ALDH and CD10. There is variable expression of CD10 on both the ALDH$^{int}$ and ALDH$^{high}$ CD34+CD38− cells.

Results. Normal donors contain CD34$^+$CD38$^-$ALDH$^{low}$ (which are nonviable) and CD34$^+$CD38$^-$ALDH$^{high}$ cell populations, but they do not have a CD34$^+$CD38$^-$ALDH$^{int}$ population (FIG. 1). However, most patients with ALL or LBC CML harbored an aberrant CD34$^+$CD38$^-$ALDH$^{int}$ population (representative pictures are shown in FIGS. 2-5). This CD34$^+$CD38$^-$ALDH$^{int}$ population was >90% positive for the BCR/ABL mutation (translocation of chromosomes 9 and 22) by FISH in all Ph+ ALL and LBC CML cases. It was similarly positive (≥75%) for other leukemia-specific FISH abnormalities (including trisomy of chromosomes 4, 8, 10, 12, and/or 21) in all ALL cases, as well as one LBC CML case (FIGS. 2-4). Notably, the CD34$^+$CD38$^-$ALDH$^{high}$ population was negative for BCR/ABL in the Ph+ ALL cases but was ≥80% positive for BCR/ABL by FISH in the LBC CML cases (FIGS. 3-4). The CD34$^+$CD38$^-$ALDH$^{high}$ population (which typically contains the normal HSCs) lacked any of the other cytogenetic abnormalities in all cases, irrespective of Ph status or a diagnosis of ALL vs. LBC CML (FIGS. 2-4).

Figure 5:
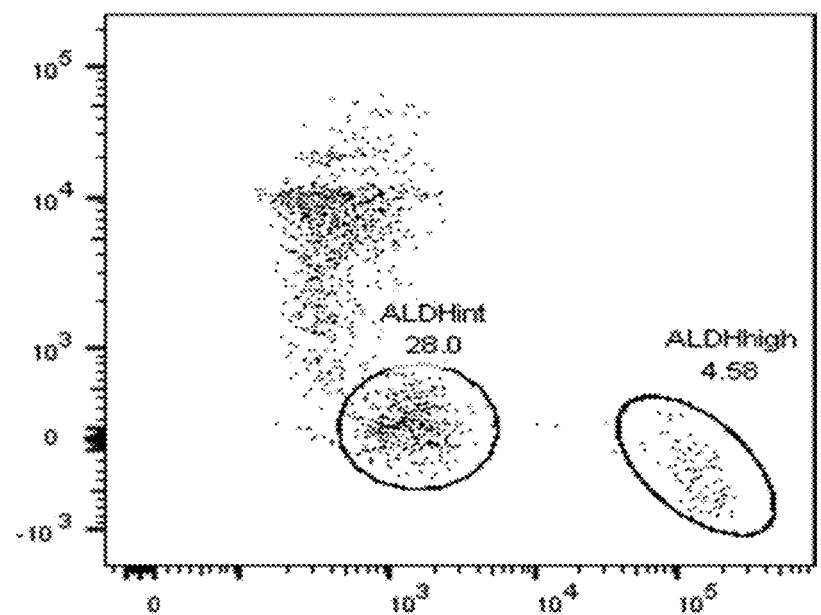
FIG. 5. Top: CD34+CD38− cells from a patient with T-cell ALL, displayed by ALDH and 7AAD (cells which are high in 7AAD and low in ALDH are nonviable). A viable, abnormal population of ALDH$^{int}$ cells (representing the putative ALL stem cell) is present. Bottom: CD34+CD38− cells displayed by ALDH and CD7. The CD34+CD38− ALDH$^{int}$ putative LSCs are positive for CD7 (circled), whereas the CD34+CD38− ALDH$^{high}$ normal HSCs (box) lack CD7.
Figure 5:
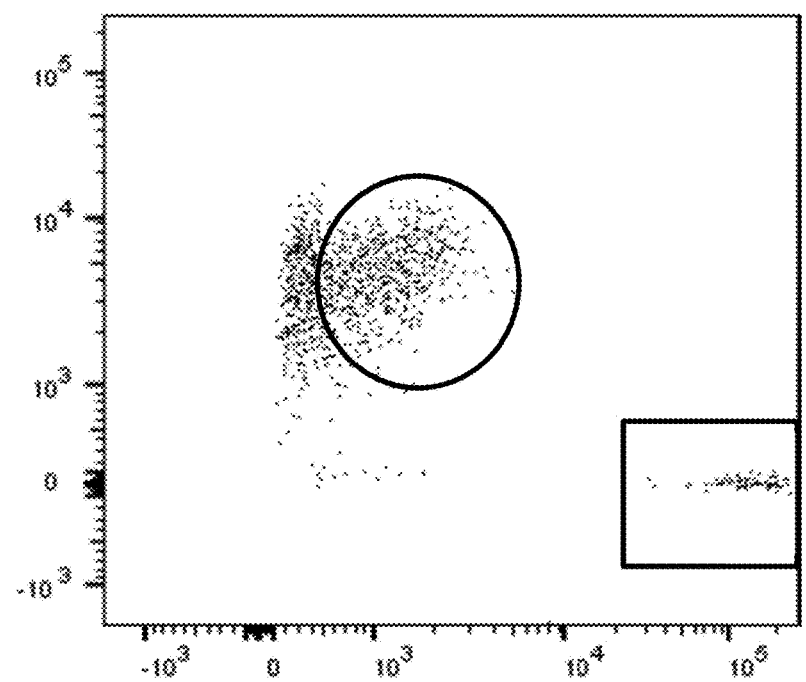

CD19 and CD10, both B-cell differentiation markers, were expressed on the CD34$^+$CD38$^-$ALDH$^{int}$ but not the CD34$^+$CD38$^-$ALDH$^{high}$ population in nearly all ALL cases, both Ph− and Ph+(FIGS. 2-3). The T-cell differentiation marker CD7 was similarly expressed on the CD34$^+$CD38$^-$ALDH$^{int}$ but not the CD34$^+$CD38$^-$ALDH$^{high}$ population in the one T-cell ALL case (FIG. 5). In contrast, CD19 and C10 expression were seen in both the CD34$^+$CD38$^-$ ALDH$^{int}$ and the CD34$^+$CD38$^-$ALDH$^{high}$ populations (FIG. 4). It appears that CD19 expression in LBC CML may distinguish abnormal, BCR/ABL positive CD34$^+$CD38$^-$ ALDH$^{high}$ cells from normal CD34$^+$CD38$^-$ALDH$^{high}$ cells in LBC CML (FIG. 4). CD10 may also prove useful in distinguishing abnormal from normal CD34$^+$CD38$^-$ALDH$^{high}$ in some cases of LBC CML, but less reliably than CD19 (FIG. 4). Of note, CD19, CD10, and CD7 were not expressed on the CD34$^+$CD38$^-$ cells of any normal donor (FIG. 1).

Figure 6:
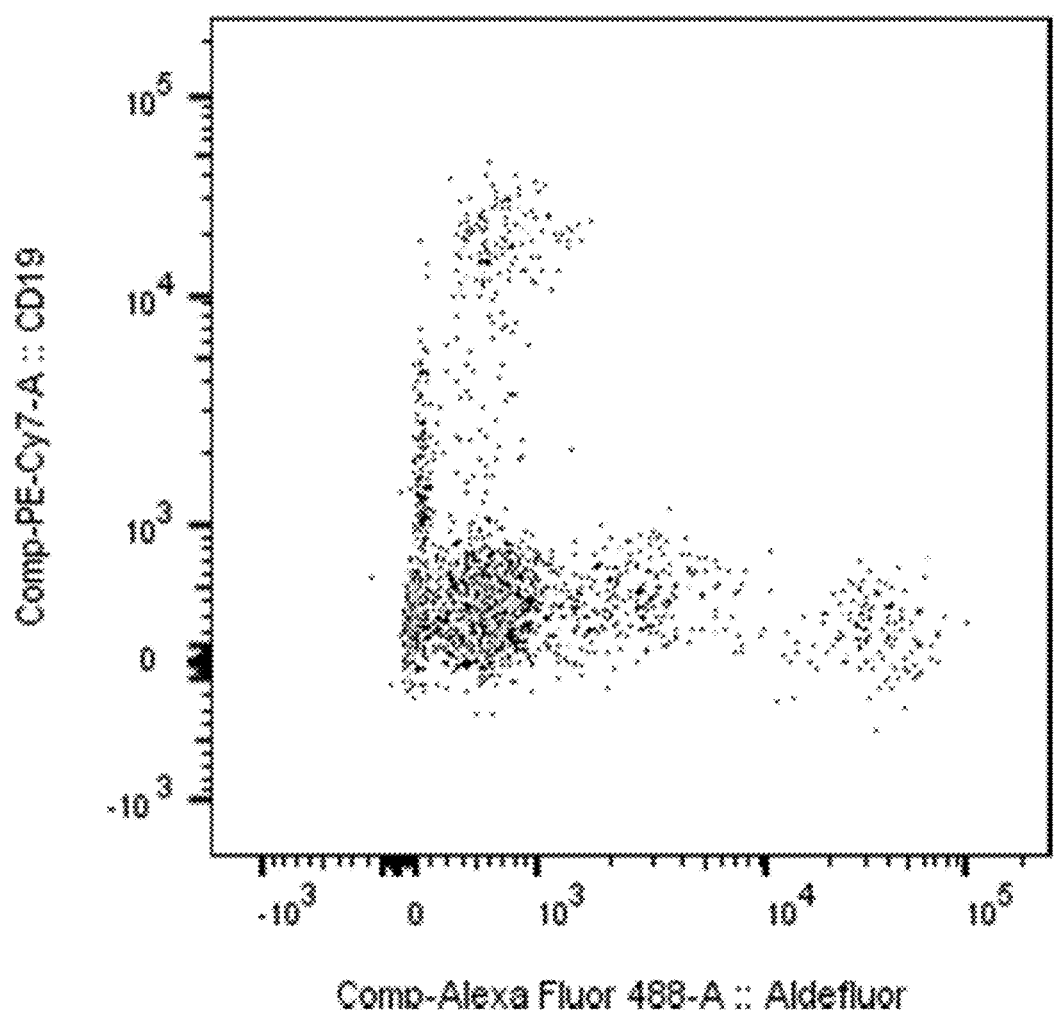
FIG. 6. CD38−, viable cells from a patient with Ph− ALL, displayed by ALDH and CD19. An abnormal population of CD38-ALDH$^{int}$ cells (representing the putative ALL stem cell) is present (circled), which is CD34− and abnormal by FISH. In contrast, a residual population of CD38-ALDH$^{high}$ cells is present (representing residual normal hematopoietic stem cells), which is CD34+ and normal by FISH (box).
Figure 7:
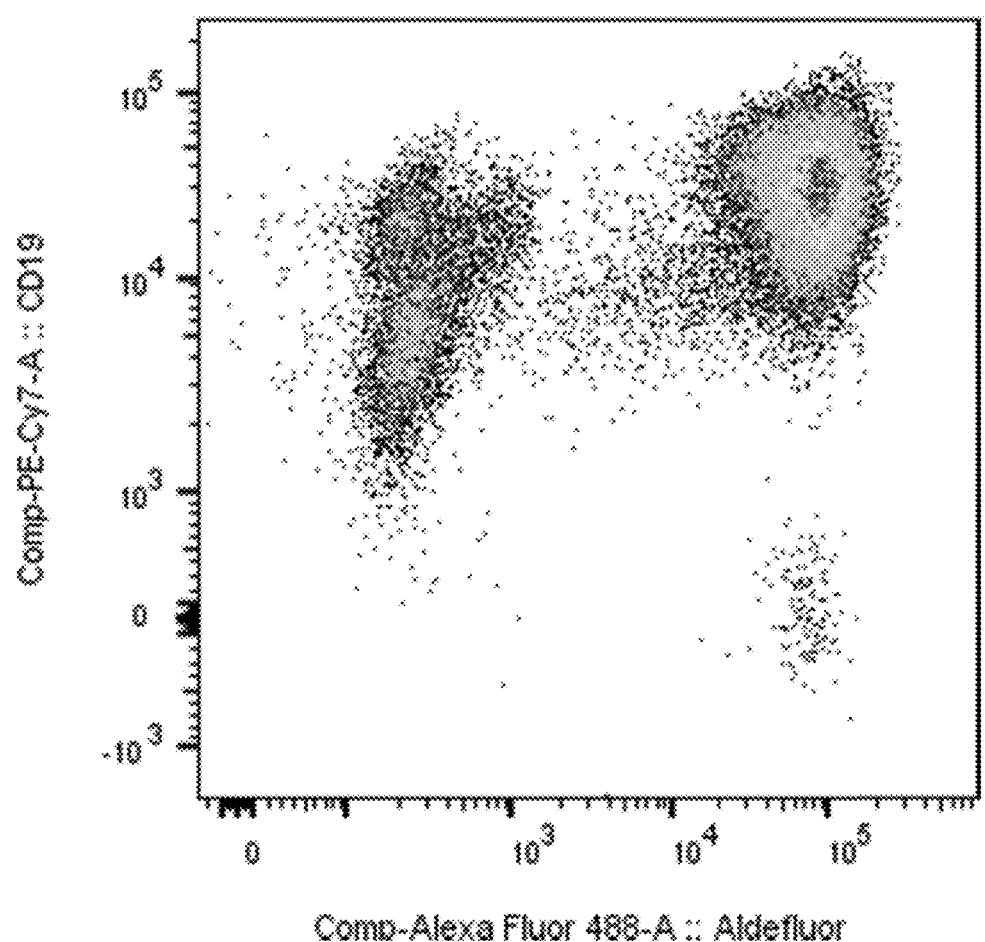
FIG. 7. CD34+CD38−, viable cells from a patient with Ph− ALL, displayed by ALDH and CD19. An abnormal population of CD34+CD38-ALDH$^{int}$ cells (representing the putative ALL stem cell) is present (circled), which is CD19+. In contrast, a residual population of CD34+CD38-ALDH$^{high}$ cells is present (representing residual normal hematopoietic stem cells), which lack CD19 (box).

One Ph− ALL case lacked any CD34$^+$ leukemic cells (FIG. 6), but still harbored an aberrant CD19$^+$CD38$^-$ALDH$^{int}$ leukemic population; all CD34$^+$ cells in this case were normal by FISH. Another Ph− ALL case harbored a CD34$^+$ CD38$^-$ALDH$^{high}$ population, which aberrantly expressed CD19; the residual normal CD34$^+$CD38$^-$ALDH$^{high}$ population in this case did not express CD19 (FIG. 7). This patient with CD19$^+$CD34$^+$CD38$^-$ALDH$^h$g$^h$ leukemia cells proved refractory even to allogeneic hematopoietic stem cell transplant.

Most of the Ph+ ALL cases possessed a p190 BCR/ABL transcript, whereas most of the LBC CML cases contained a p210 transcript.

Figure 8:
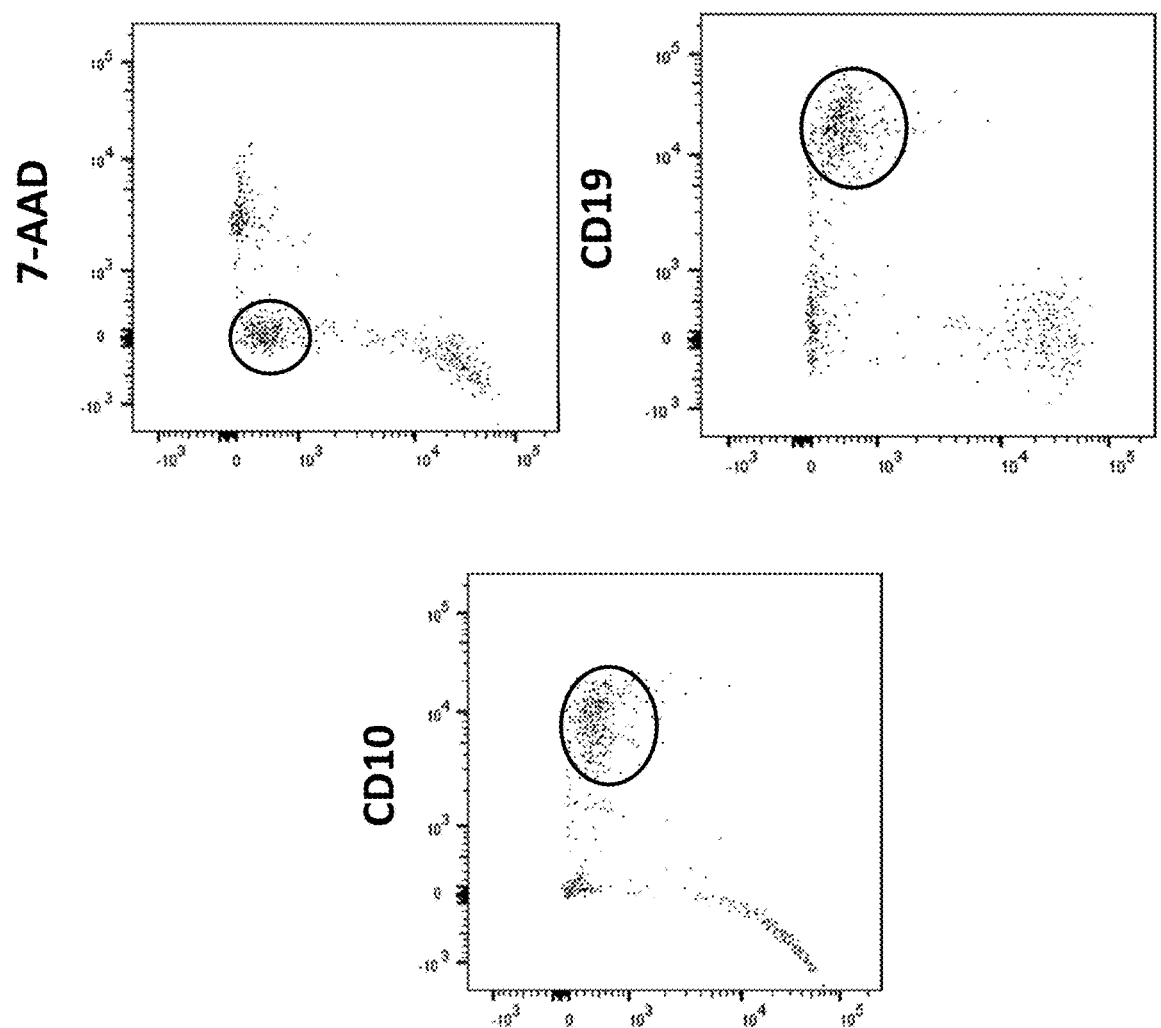
FIG. 8. CD34+CD38− cells from a patient with Ph− ALL following therapy. Clinical flow cytometry detected minimal residual disease (MRD) present at 0.062% of the total mononuclear bone marrow cells. Left: CD34+CD38− cells displayed by ALDH and 7AAD (cells which are high in 7AAD and low in ALDH are nonviable). A viable, abnormal ALDH$^{int}$ population (circled), representing putative ALL stem cells, persists after therapy. This population constitutes 44% of the total CD34+CD38− cells and 64.5% of the total viable CD34+CD38− cells. This represents a roughly 1,000-fold enrichment of the leukemic cells vs. the currently available clinical testing, suggesting that MRD is disproportionately composed of LSCs (i.e., LSCs are more resistant to therapy than are the bulk leukemic cells) and that the proposed LSC assay potentially has far more sensitivity than existing clinical tests. Center: The persistent CD34+CD38− ALDH$^{int}$ putative LSCs (circled) are positive for CD19, whereas the CD34+CD38− ALDH$^{high}$ normal HSCs lack CD19. This suggests that therapies which target CD19 might be capable of eradicating MRD and potentially achieving cure in this patient. Right: The CD34+CD38− ALDH$^{int}$ putative LSCs (circled) are also positive for CD10, whereas the CD34+CD38− ALDH$^{high}$ normal HSCs lack CD10. This suggests that therapies which target CD10 might be capable of eradicating MRD and potentially achieving cure in this patient.
Figure 9:
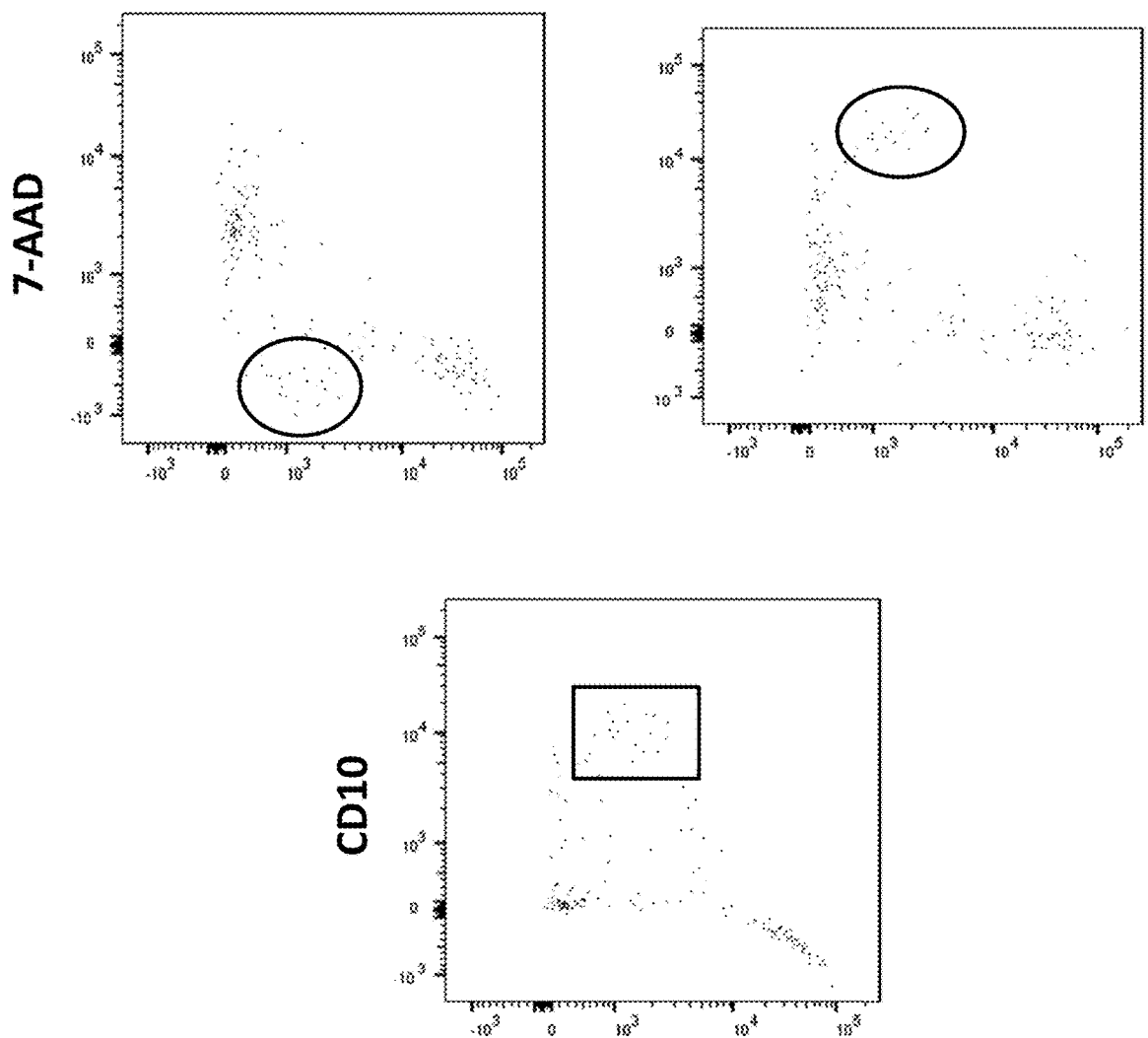
FIG. 9. CD34+CD38− cells from a patient with Ph+ ALL following therapy. Clinical flow cytometry detected borderline positive minimal residual disease (MRD) at <0.01% of the total mononuclear bone marrow cells, and PCR testing for the BCR/ABL mutation was positive for low levels of MRD at 0.014%. Left: CD34+CD38− cells displayed by ALDH and 7AAD (cells which are high in 7AAD and low in ALDH are nonviable). A viable, abnormal ALDH$^{int}$ population (circled), representing putative ALL stem cells, persists after therapy. This population constitutes 7% of the total CD34+CD38− cells and roughly 20% of the total viable CD34+CD38− cells. This represents an approximately 1,000-fold enrichment of the leukemic cells vs. the currently available clinical testing, suggesting that MRD is disproportionately composed of LSCs (i.e., LSCs are more resistant to therapy than are the bulk leukemic cells) and that the proposed LSC assay potentially has far more sensitivity than existing clinical tests. Center: The persistent CD34+CD38− ALDH$^{int}$ putative LSCs (circled) are positive for CD19, whereas the CD34+CD38− ALDH$^{high}$ normal HSCs lack CD19. This suggests that therapies which target CD19 might be capable of eradicating MRD and potentially achieving cure in this patient. Right: The CD34+CD38− ALDH$^{int}$ putative LSCs (circled) are also positive for CD10, whereas the CD34+CD38− ALDH$^{high}$ normal HSCs lack CD10. This suggests that therapies which target CD10 might be capable of eradicating MRD and potentially achieving cure in this patient.

The proposed LSC assay appeared to be more sensitive than existing clinical tests for minimal residual disease (MRD). Two representative MRD samples are shown in FIGS. 8-9. In the first case (FIG. 8), clinical MRD flow cytometry testing revealed an abnormal (leukemic) population constituting 0.062% of the total mononuclear bone marrow cells. In contrast, the proposed LSC assay detected an (abnormal) CD34$^+$CD38$^-$ALDH$^{int}$ population constituting 44% of the total and 64.5% of the viable CD34$^+$CD38$^-$ cells. In the second case, clinically available MRD testing was positive at low levels: at <0.01% of the total mononuclear bone marrow cells by flow cytometry and at 0.014% by PCR testing for the BCR/ABL mutation. However, the proposed LSC assay detected an (abnormal) CD34$^+$CD38$^-$ ALDH$^{int}$ population constituting 7% of the total CD34$^+$CD38$^-$ cells and roughly 20% of the viable CD34$^+$CD38$^-$ cells. Analogous to results seen with existing clinical MRD testing, the presence of a persistent CD34$^+$CD38$^-$ALDH$^{int}$ population after therapy appears to correlate with a higher risk of relapse.

Conclusions. An abnormal CD34$^+$CD38$^-$ALDH$^{int}$ population was identified in most cases of B-cell ALL, LBC CML, and the only case of T-cell ALL. This population may represent a putative LSC population in ALL. This technique can be used to separate normal HSCs (which are CD34$^+$ CD38$^-$ALDH$^{high}$ and lack additional markers such as CD19, CD10, and/or CD7) from LSCs (which are typically CD34$^+$ CD38$^-$ALDH$^{int}$ and may also express CD19+, CD10+, CD7+ and/or additional, as yet unidentified, markers) in ALL. The CD34$^+$CD38$^-$ALDH$^{high}$ population was normal by FISH in the ALL cases but contained the BCR/ABL mutation in the LBC CML cases, thus permitting distinction between Ph+ ALL and LBC CML (which also differed based on the presence of p190 vs. p210 transcripts, respectively). Additionally, clonal evolution from chronic phase to lymphoid blast crisis CML was apparent, based on the acquisition of additional cytogenetic abnormalities unique to the CD34$^+$CD38$^-$ALDH$^{int}$ population as compared to the CD34$^+$CD38$^-$ALDH$^{high}$ population (as seen in FIG. 4).

The presence of CD19 on the putative LSCs in ALL and LBC CML suggest that CD19-directed therapies may target the LSCs and thus may have curative potential in those cases. This assay may serve as a means to identify other possible therapeutic targets and to assess the efficacy of therapies against the LSCs (and hence the curative potential of such therapies).

Additionally, the various LSC phenotypes identified may correlate with prognosis.

Lastly, the detection of the abnormal LSC CD34$^+$CD38$^-$ ALDH$^{int}$ population (potentially in combination with other markers, such as CD19+, CD10+, CD7+ and/or other markers) may have utility as a MRD assay for monitoring response to treatment and predicting relapse. In fact, the proposed LSC assay provides a roughly 1,000-fold enrichment of the leukemic cells vs. the currently available clinical MRD testing, suggesting that the proposed LSC assay potentially has far more sensitivity than existing clinical tests. Interestingly, the fact that MRD is disproportionately composed of LSCs implies that the LSCs are more resistant to therapy than are the bulk leukemic cells and that the LSCs need to be eradicated to achieve cure.

While there are shown and described particular embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

That which is claimed is:

1. A method of guiding treatment of a subject having or diagnosed with acute lymphocytic leukemia (ALL) or lymphoid blast crisis chronic myeloid leukemia (LBC CML) at increased risk of relapse after chemotherapy alone, comprising:
   (a) obtaining a biological cell sample from the subject;
   (b) isolating mononuclear cells from the sample of (a);
   (c) allowing the cells of (b) to take up a fluorescence substrate for the enzyme aldehyde dehydrogenase (ALDH) and labeling the cells with an anti-CD34 monoclonal antibody and an anti-CD38 monoclonal antibody, in combination with an anti-CD19 monoclonal antibody;
   (d) isolating $CD34^+CD38^-$ mononuclear cells from the cells of (c) using flow cytometry;
   (e) measuring the ALDH activity of the cells of (d);
   (f) comparing the levels of ALDH activity in the cells of (e) with the levels of ALDH activity in the cells of a reference sample; and
   (g) identifying cells of (f) that have a high level of ALDH activity ($CD34^+CD38^- ALDH^{high}$) in the sample from the subject when compared to the level of ALDH activity of the $CD34^+CD38^-$ cells in the reference sample; and
   h) assaying the $CD34^+CD38^-ALDH^{high}$ cells identified in (g) for the presence or absence of CD19 on the surface of the $CD34^+CD38^-ALDH^{high}$ cells, wherein the presence of CD19 cells on the surface of the $CD34^+CD38^-ALDH^{high}$ cells identifies the subject as being more likely to relapse after chemotherapy alone relative to a subject lacking said cells; and
   (i) administering a treatment to the subject, selected from immunotherapy, an anti-body based therapy, hematopoietic stem cell transplantation, and/or chimeric antigen receptor T cell therapy with or without chemotherapy to decrease the subject's risk of relapse.

2. The method of claim 1, further comprising assaying the cells of (d) for the presence or absence of CD3, CD5, CD20, CD22, CD25, CD33, CD40, CD42, CD44, CD45, CD47, CD90, CD96, CD123, CD133, CD138, CD235a, IL1RAP, PD1, and/or PDL1 on the cells.

* * * * *

UNITED STATES PATENT AND TRADEMARK OFFICE
CERTIFICATE OF CORRECTION

PATENT NO. : 10,222,376 B2
APPLICATION NO. : 15/796201
DATED : March 5, 2019
INVENTOR(S) : Jonathan M. Gerber Page 1 of 1

It is certified that error appears in the above-identified patent and that said Letters Patent is hereby corrected as shown below:

In the Specification

Column 5, Line 17: Please correct "stein cell" to read -- stem cell --

Column 10, Line 48: Please correct "CD38''" to read -- $CD38^-$ --

Column 15, Line 22: Please correct "ALDHn" to read -- $ALDH^{int}$) --

Column 22, Line 8: Please correct "$ALDH^hg^h$" to read -- $ALDH^{high}$ --

In the Claims

Column 24, Line 11, Claim 1: Please correct "$CD38^{31}$" to read -- $CD38^-$ --

Signed and Sealed this
Twenty-fifth Day of June, 2019

Andrei Iancu
*Director of the United States Patent and Trademark Office*